US010076246B2

(12) United States Patent
Jerosch-Herold et al.

(10) Patent No.: US 10,076,246 B2
(45) Date of Patent: Sep. 18, 2018

(54) METHOD AND APPARATUS FOR NONINVASIVE QUANTITATIVE DETECTION OF FIBROSIS IN NORMAL AND VIABLE MYOCARDIUM BY MRI

(71) Applicants: Michael Jerosch-Herold, Lexington, MA (US); Sumeet S. Chugh, Los Angeles, CA (US)

(72) Inventors: Michael Jerosch-Herold, Lexington, MA (US); Sumeet S. Chugh, Los Angeles, CA (US)

(73) Assignee: Oregon Health & Science University, Portland, OR (US)

( * ) Notice: Subject to any disclaimer, the term of this patent is extended or adjusted under 35 U.S.C. 154(b) by 1091 days.

(21) Appl. No.: 13/910,450

(22) Filed: Jun. 5, 2013

(65) Prior Publication Data

US 2013/0267828 A1  Oct. 10, 2013

Related U.S. Application Data

(63) Continuation of application No. 12/595,567, filed as application No. PCT/US2008/060020 on Apr. 11, 2008, now abandoned.

(Continued)

(51) Int. Cl.
*A61B 5/00* (2006.01)
*A61B 6/03* (2006.01)
(Continued)

(52) U.S. Cl.
CPC .......... *A61B 5/0044* (2013.01); *A61B 5/0035* (2013.01); *A61B 5/055* (2013.01);
(Continued)

(58) Field of Classification Search
None
See application file for complete search history.

(56) References Cited

U.S. PATENT DOCUMENTS 6,045,775 A  4/2000 Ericcson et al.
6,205,349 B1  3/2001 Kim et al.
(Continued)

OTHER PUBLICATIONS

Saeed et al, T1-relaxation kinetics of extracellular, intracellular and intravascular MR contrast agents in normal and acutely reperfused infarcted myocardium using echo-planar MR imaging, Eur. Radiol. 10, 310-318, 2000.*

(Continued)

*Primary Examiner* — Serkan Akar
(74) *Attorney, Agent, or Firm* — Schwabe, Williamson & Wyatt, P.C.

(57) ABSTRACT

Embodiments provide a noninvasive quantitative method for detecting extent and/or types of fibrosis in the heart. In embodiments, information pertaining to the extent and/or types of fibrosis may aid in the diagnosis of specific cardiac diseases and heart failure and/or may assist in determining suitable treatment options. Embodiments provide methods and apparatuses for determining the extent of fibrosis in viable and nonviable myocardium, which may then be correlated to heart disease and failure. Thus, in an embodiment, a method of screening individuals for the purpose of heart disease or heart failure prevention may be provided using the detection methodology described herein.

11 Claims, 3 Drawing Sheets

Related U.S. Application Data (60) Provisional application No. 60/911,110, filed on Apr. 11, 2007.

(51) Int. Cl.
| | |
|---|---|
| *A61K 49/06* | (2006.01) |
| *A61B 5/055* | (2006.01) |
| *G06T 7/00* | (2017.01) |
| *A61B 5/026* | (2006.01) |
| *A61B 5/0275* | (2006.01) |
| *A61B 6/00* | (2006.01) |
| *G01R 33/28* | (2006.01) |
| *G01R 33/56* | (2006.01) |

(52) U.S. Cl.
CPC ............... *A61B 6/03* (2013.01); *A61K 49/06* (2013.01); *G06T 7/0012* (2013.01); *A61B 5/0263* (2013.01); *A61B 5/0275* (2013.01); *A61B 6/503* (2013.01); *A61B 6/504* (2013.01); *G01R 33/281* (2013.01); *G01R 33/5602* (2013.01); *G06T 2207/10076* (2013.01); *G06T 2207/10088* (2013.01); *G06T 2207/30024* (2013.01); *G06T 2207/30048* (2013.01)

(56) References Cited

U.S. PATENT DOCUMENTS

| | | |
|---|---|---|
| 6,972,122 B2 | 12/2005 | Haroon et al. |
| 7,206,629 B2 | 4/2007 | Graessner |
| 7,208,138 B2 | 4/2007 | Haroon et al. |
| 7,208,139 B2 | 4/2007 | Platzek et al. |
| 7,408,546 B2 | 8/2008 | Serra |
| 7,966,056 B2 | 6/2011 | Rongved et al. |
| 2002/0087067 A1 | 7/2002 | Foo |
| 2002/0090341 A1 | 7/2002 | Watson et al. |
| 2002/0136692 A1 | 9/2002 | Haroon et al. |
| 2003/0064024 A1 | 4/2003 | Driehuys et al. |
| 2003/0069496 A1 | 4/2003 | Foo |
| 2005/0065430 A1 | 3/2005 | Wiethoff |
| 2005/0165290 A1 | 7/2005 | Kotsianti et al. |
| 2005/0215883 A1 | 9/2005 | Hundley et al. |
| 2006/0025815 A1 | 2/2006 | McGurk et al. |
| 2006/0083689 A1 | 4/2006 | Haroon et al. |
| 2006/0235292 A1 | 10/2006 | Rongved et al. |
| 2007/0042016 A1 | 2/2007 | Nayak et al. |
| 2010/0129292 A1 | 5/2010 | Jerosch-Herold et al. |

OTHER PUBLICATIONS

John et al., "Global Remodeling of the Ventricular Interstitium in Idiopathic Myocardial Fibrosis and Sudden Cardiac Death," Heart Rhythm (2004) 1, 141-149.

"Kim, Raymond J. et al., ""The Use of Contrast-Enhanced Magnetic Resonance Imaging to Identify Reversible Myocardial Dysfunction,"" The New England Journal of Medicine, Nov. 16, 2000, vol. 343, No. 20; pp. 1445-1453; 860 Winter Street, Waltham, MA 02451-1413".

Klein, et al., "The Influence of Myocardial Blood Flow and Volume of Distribution on Late GD-DTPA Kinetics in Ischemic Heart Failure," Journal of Magnetic Resonance Imaging 20:588-594 (2004).

Knaapen et al., "Perfusable Tissue Index as a Potential Marker of Fibrosis in Patients with Idiopathic Dilated Cardiomyopathy," The Journal of Nuclear Medicine, vol. 6, No. 8, Aug. 2004.

Kroll et al., "Modeling Regional Myocardial Flows from Residue Functions of an Intravascular Indicator," Am. J. Physiol. Oct. 1996; 271 (4 Pt 2): H1643-H1655).

Paetsch, et al., "Myocardial Perfusion Imaging Using OMNISCAN: A Dose Finding Study for Visual Assessment of Stress-Induced Regional Perfusion Abnormalities," Journal of Cardiovascular Magnetic Resonance, vol. 6, No. 4, pp. 803-809, 2004.

Tandri, Harikrishna et al., "Noninvasive Detection of Myocardial Fibrosis in Arrhythmogenic Right Ventricular Cardiomyopathy Using Delayed-enhancement Magnetic Resonance Imaging," Journal of the American College of Cardiology, 2005; vol. 45, No. 1; pp. 98-103, 3655 Nobel Drive Suite 630, San Diego CA 92122.

\* cited by examiner

METHOD AND APPARATUS FOR NONINVASIVE QUANTITATIVE DETECTION OF FIBROSIS IN NORMAL AND VIABLE MYOCARDIUM BY MRI

CROSS REFERENCE TO RELATED APPLICATIONS

The present application is a continuation of U.S. patent application Ser. No. 12/595,567, filed Oct. 12, 2009, which is a U.S. National Phase Application of PCT/US2008/060020, filed Apr. 11, 2008, which claims priority to U.S. Provisional Patent Application No. 60/911,110, filed Apr. 11, 2007, the entire disclosures of which are hereby incorporated by reference in their entirety.

TECHNICAL FIELD

Embodiments relate to the field of medical diagnostics and monitoring, and, more specifically, to a method and apparatus for noninvasive quantitative detection of both diffuse and focal fibrosis in the heart.

BACKGROUND

Myocardial fibrosis is a morphologic change common to multiple cardiac disease conditions. In addition to replacement (scar) fibrosis, there is increasing recognition of interstitial (reactive) fibrosis being an important player in structural remodeling of the diseased heart, as well as the genesis of fatal arrhythmia leading to sudden cardiac death. Currently, fibrosis is quantified by histochemical analysis of tissue samples obtained by surgical biopsy. The availability of a non-invasive test to quantify replacement and interstitial fibrosis, which may be correlated with the collagen volume fraction (CVF), would be a significant advance.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 1 illustrates inversion recovery signal intensity curves. For determination of the contrast agent partition coefficient, T1 was quantified for user-defined regions of interest in the heart. A software program was used to load the DICOM-format MRI images for a series of 12 to 17 inversion times, and fit inversion recovery signal intensity curves, as shown for two regions in FIG. 1, were generated to determine T1. This analysis was performed twice, first for measurements of T1 before contrast enhancement, and then after incubation of the samples in a gadolinium contrast agent solution for 24 hours. The graph shows differences in regional T1 after placing the sample in the contrast agent solution, and the area with the shorter T1 (posterior lateral region) corresponds to a region with marked fibrosis.

FIG. 2A shows a post-mortem T1-weighted MRI image of a heart slice (patient with cardiomegaly, and extensive atherosclerosis) after 24 hour incubation in contrast agent (gadodiamide) solution. The inversion time of 300 ms resulted in a contrast, such that tissue with higher gadodiamide distribution volume appears brighter. FIG. 2B shows a histological image of the same myocardial slice stained and showing extensive fibrosis in posterior-lateral areas, matching those with increased signal intensity on the MRI image.

DETAILED DESCRIPTION OF DISCLOSED EMBODIMENTS

In the following detailed description, reference is made to the accompanying drawings which form a part hereof, and in which are shown by way of illustration various embodiments. It is to be understood that other embodiments may be utilized and structural or logical changes may be made without departing from the intended scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, left/right, and top/bottom. Such descriptions are merely used to facilitate the discussion and are not intended to restrict the application of the embodiments.

For the purposes of the description, a phrase in the form "A/B" or in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to various embodiments, are synonymous.

In various embodiments, methods, apparatuses, and systems for determining the presence and extent of fibrosis in myocardial tissue are provided. In exemplary embodiments, a computing system may be endowed with one or more components of the disclosed apparatuses and/or systems and may be employed to perform one or more methods as disclosed herein.

Embodiments provide a noninvasive quantitative method for detecting the extent and/or types of fibrosis in the heart. In embodiments, information pertaining to the extent and/or types of fibrosis may aid in the diagnosis of specific cardiac diseases and heart failure and/or may assist in determining suitable treatment options. Embodiments provide methods and apparatuses for determining the extent of fibrosis in viable and nonviable myocardium, which may then be correlated to heart disease and failure. Thus, in an embodiment, a method of screening individuals for the purpose of heart disease or heart failure prevention may be provided using the detection methodology described herein.

In an embodiment, a method allows for the detection and quantification of cardiac fibrosis using contrast enhanced magnetic resonance imaging (MRI) (or another imaging method such as computed tomography) as an alternative to histological evaluation. In an embodiment, a method provides for measurement of the myocardial partition coefficient for an extracellular contrast agent, showing the relative distribution volume of the contrast agent, which may be used to quantify diffuse, reactive, interstitial, or replacement fibrosis, conditions that may be inadequately detected by current methods. All forms of fibrosis lead to an expansion of the extracellular matrix, which in turn increases the volume accessible to extracellular contrast agents, such as gadiodiamide in the case of MRI. Embodiments may be applied to in-vitro and in-vivo evaluation.

MRI of delayed contrast enhancement (DCE) with an extracellular contrast agent, such as gadodiamide-DTPA, has become a desirable method to depict non-viable myocardium with high spatial resolution. DCE MRI relies on the detection of contrast enhancement relative to other remote areas in the same heart. In cardiac diseases such as non-ischemic dilated cardiomyopathies with evidence from histology of diffuse fibrosis, current non-invasive tests, including those based on cardiac MRI, may fail in detecting this diffuse, generalized fibrosis. Focal areas of delayed contrast enhancement may be either absent, or only provide a partial measure of fibrosis extent and burden. Embodiments disclosed herein provide a novel approach, whereby the relative distribution volume of contrast agent, and/or the myocardial partition coefficient for the contrast agent, is determined to obtain a quantitative measure of the extracellular volume fraction as a marker of fibrosis in viable or nonviable myocardium. In viable myocardium, the myocardial partition coefficient is proportional to the extracellular volume fraction. In an embodiment, the extracellular volume fraction may be quantified with MRI by determining the change of R1 relaxation rate constants in tissue and blood, respectively, both before and after administration of the contrast agent. Alternatively, in an embodiment, one may employ a dynamic imaging method to measure signal changes observed with a heavily T1-weighted pulse sequence between the pre-contrast and post-contrast states.

In an embodiment, the measurement of the myocardial partition coefficient for certain contrast agents, such as Gd-DTPA, is suitable for differentiating extent of myocardial fibrosis on a continuous scale, spanning the range from normal myocardium, through diffuse interstitial and replacement fibrosis in viable myocardium, to non-viable fibrotic scar tissue.

For quantification of the tissue partition coefficient, the myocardial partition coefficient for a contrast agent is defined as the ratio of the contrast agent concentrations in tissue and blood, at equilibrium. At equilibrium, the concentration of an extracellular contrast agent within the interstitial space should equal the plasma concentration. In terms of the specific volumes (volumes normalized by tissue weight, expressed as ml/g of tissue) of the interstitial ($v_{isf}$) and plasma spaces ($v_p$) one may express the partition coefficient for an extracellular contrast agent as:

$$\lambda = \frac{v_{isf} + v_p}{(1 - Hct)}, \quad (1)$$

where Hct is the blood hematocrit. An MRI contrast agent is typically detected through its effect on the $^1H$ MR signal. The signal from the blood constituents, plasma, and erythrocytes, is characterized by a single relaxation rate due to fast exchange of water between plasma and erythrocytes—the intracellular lifetime of water inside erythrocytes is ~10 ms under physiological conditions.

Various strategies have been devised to measure the myocardial partition coefficient for extracellular contrast agents with MRI, which were focused almost exclusively on studies in healthy volunteers, or in patients with ischemic heart disease and myocardial necrosis. The myocardial partition coefficient may be calculated from the change of R1 (R1=1/T1) in tissue, divided by the change of R1 in the blood pool. Alternatively, one may measure signal changes with pulse sequences producing strong T1-weighting.

In an embodiment, the distribution volume of certain contrast agents may be elevated in myocardium with even mild interstitial fibrosis. In addition, in an embodiment, the distribution volume may be linearly related to the CVF, an established histological quantification of myocardial fibrosis.

In an embodiment, a suitable contrast agent may be an extracellular contrast agent or a collagen binding agent. In an embodiment, a suitable contrast agent may be Gadolinium or a Gadolinium-based compound, such as gadodiamide.

In an embodiment, an in-vitro MRI technique is provided for comparison of contrast agent distribution volume as a measure of both replacement and interstitial myocardial fibrosis, with a histologically determined myocardial CVF, the current gold standard for quantification of myocardial fibrosis. In an embodiment, the MRI measures of fibrosis may correlate significantly with CVF supporting the suitability of the new methodology. Using ex-vivo myocardial tissue samples, it may be observed that gadodiamide MRI differentiates between normal myocardium, and interstitial (reactive) fibrosis, and between normal myocardium and replacement (scar) fibrosis. In accordance with an embodiment, the contrast distribution volume and CVF also vary significantly across fibrosis categories, namely normal, interstitial and replacement fibrosis, allowing for types of fibrosis to be distinguished as well. Embodiments use MRI to derive a quantitative measure of fibrosis, which correlates with CVF in myocardial tissue.

Following acute myocardial infarction, MRI of delayed contrast hyper-enhancement with gadodiamide-contrast reflects the breakdown of the cell-membrane, which increases the volume of distribution of gadodiamide-contrast relative to viable myocardium. In areas of myocardial infarction, a dense collagen matrix leads to focal hyper-enhancement relative to areas with viable myocardium. In a canine model of chronic myocardial infarction with dense collagen matrix within the infarct zone, it has been shown that contrast hyper-enhancement was similar to the hyper-enhancement observed in acute infarcts. Other causes of increased myocardial fibrosis have also been shown to lead to increased gadodiamide-contrast uptake compared to normal tissue.

Currently, total CVF is the most widely used measure of fibrosis burden. Essentially two methods exist to determine total CVF: an absolute measure using hydroxyproline to bind collagen and segregate it from other tissue constituents, and a measurement of CVF that uses tissue staining and photometry. Embodiments herein provide contrast-enhanced MRI as a semi-quantitative method of measuring CVF that extends beyond traditional CVF and histological analysis. The correlation between CVF and MRI described herein allows for comparison between data observed between the two methods. In addition, due to the non-invasive nature of MRI, various disclosed embodiments may reduce the need for endocardial biopsies.

Although the contrast distribution volume estimate from MRI and CVF from a photometric assay correlate well, the underlying methods have some significant differences worth noting. The photometry-based determination of CVF requires the selection of small (approximately 40 mm$^2$) areas under a microscope for the pixel count, and the resulting CVF estimate may not be representative of a wall segment. With MRI, the region of interest is user-defined, at a much lower magnification scale and signal-averages for arbitrarily-sized regions are readily calculated for each image. This difference between the CVF measurement and the MRI method is analogous to a biopsy-based measurement compared to an imaging-based measurement. While the first represents an often arbitrary and restricted choice of tissue within the heart, the latter may be freely specified by an observer, assuming good image quality and spatial resolution.

As an example of the above-described methodology, eight samples of human myocardium were obtained postmortem and a fast spin-echo sequence (3 Tesla) with non-slice selective inversion pulse performed before and after immersion in a gadodiamide saline solution for determination of the gadodiamide partition coefficient. T1 values were calculated from the inversion recovery signal curves. The same samples were fixed in formalin, and the collagen volume fraction was determined by the picrosirius red method using a semi-automated, polarized, digital microscopy system. The results showed that both gadodiamide distribution volumes as well as CVF values were significantly different in normal myocardium vs. interstitial fibrosis (p=0.001), and normal vs. replacement fibrosis (p=0.015). Moreover, there was a significant positive correlation between the two methods, across all three histological categories of myocardial fibrosis (r=0.73; p=0.017). Thus, these findings indicate an expanded potential for contrast enhanced MRI as a novel, non-invasive alternative to histological evaluation, for the quantification of both interstitial and replacement myocardial fibrosis.

In accordance with an exemplary embodiment as outlined briefly above, eight samples of myocardium were obtained from deceased patients. Each sample of ventricular myocardium was 1 to 2 cm in thickness, and cut at the mid-level of the ventricular septum to include left and right ventricular free walls. All samples were stored at $-80°$ C. until time of analysis.

A pre-contrast MRI was performed approximately 10-12 hours after thawing each sample. The samples were brought to room temperature before each MRI measurement. The longitudinal relaxation time T1 of myocardial tissue and saline was measured with a spin-echo MRI pulse sequence with non-slice-selective inversion pulse, and for 12-15 inversion delays (inversion times in the range from T1=50 to 2000 ms). The other sequence parameters were: repetition time (TR)=2500 ms, echo-time (TE)=9.5 ms, slice thickness of 2.5 mm, receiver bandwidth=190 Hz/pixel, and image matrix=256 by 256. For each sample, a beaker with the tissue sample immersed in saline was placed in a small radio-frequency coil designed for wrist imaging, and all images were acquired at 3 Tesla (Siemens Trio, Siemens Medical Solutions, Malvern, Pa.).

After the first MRI scan, the sample was incubated at 3-4° C. in a gadodiamide—saline solution for 24 hours (initial gadodiamide concentration in saline before immersion of tissue slice was ~3 mM; saline R1 at 3 Tesla after 24 hours incubation: 3.9±0.3 s$^{-1}$). The gadodiamide contrast agent (Omniscan; GE-Healthcare, Princeton, N.J.) has an osmolality at 37° C. of 789 (mOsmol/kg water). A second post-contrast MRI was then performed, with identical sequence parameters as for the first measurement. The effects of duration of thawing were also evaluated. Two tissue samples remained thawed for 60 hours before the second MRI was performed. All other tissue samples were kept in a temperature range from 3-4° C. during gadodiamide incubation and room temperature for 32 hours before the second MRI. Thawing time is potentially important because the integrity of the cell membranes degrades during the time the tissue is not frozen. Accordingly, these two sets of samples with different durations of thawing were analyzed separately.

For image analysis, a custom software program was written to load the images for different inversion time values in DICOM format, and determine T1 from the inversion recovery signal curves for myocardial tissue and saline, both with and without gadodiamide contrast, by use of a non-linear least-squares fitting algorithm (Matlab version 6.5, The Mathworks, Natick, Mass.). Changes in the relaxation rate R1 (R1=1/T1) are proportional to the local concentration of gadodiamide in tissue. The gadodiamide-contrast partition coefficient was calculated as:

$$\lambda = \frac{1/R_1^{tissue}(\text{post-contrast}) - 1/R_1^{tissue}(\text{pre-contrast})}{1/R_1^{saline}(w/Gd) - 1/R_1^{tissue}(w/oGd)} \quad (2)$$

Figure 1:
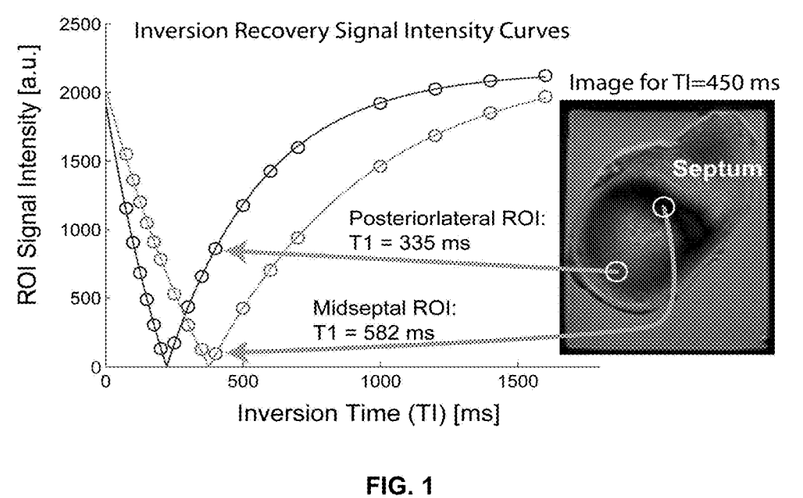

For ex-vivo measurements of tissue in saline, the measured partition coefficient was equated to the relative distribution volume, assuming that the gadodiamide contrast concentration reached an equilibrium state after 24 hours incubation of tissue slices in gadodiamide solution. FIG. 1 is an example of an MRI image of a sample.

After MRI analysis, the samples were preserved in formalin. The formalin fixed tissue was then processed, embedded in paraffin and sections prepared of the entire surface area of the sample including septum, left ventricular free wall and right ventricular free wall. The sections, 5 microns in thickness, were stained with picrosirius red and viewed under polarized light at 40× power.

Figure 2A:
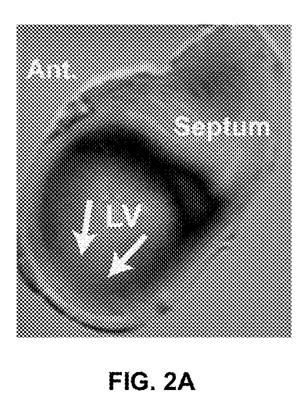
FIGS. 2A and 2B illustrate heart slice images.
Figure 2B:
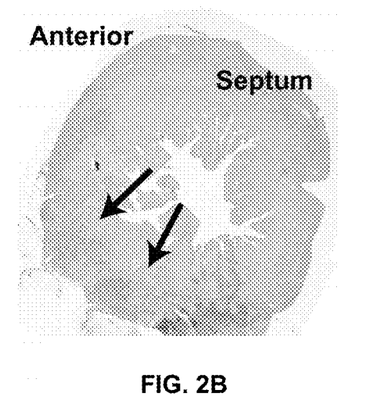

Two investigators independently analyzed all 8 samples under low (10×) magnification. Samples were classified as either entirely normal, or containing areas with abnormal distribution and content of collagen. Abnormal samples were further subdivided into those having interstitial (reactive) fibrosis, or as having replacement fibrosis. In samples with areas of fibrosis, a remote region without fibrosis or abnormal collagen distribution was also identified. 15 regions of interest were identified within the 8 samples, with one completely normal sample only containing one region. The areas identified were viewed under 40× magnification and CVFs were determined. FIG. 2 shows a stained sample and a corresponding MRI image, with matching areas identified by arrows.

Areas of interest, as mentioned above, were identified histologically on the paraffin-embedded slices. Matching locations were identified on the MRI images by using anatomical landmarks such as the insertion of the right ventricle into the left ventricle, or papillary muscles. Given the differences in tissue size and shape between fresh tissue and paraffin embedded tissue, in an embodiment, locations are estimated to be matched with an accuracy of approximately ±1 cm in the circumferential direction, and approximately ±0.5 cm in the radial direction.

CVF is a computer assisted quantification of myocardial fibrosis in histological sections widely used for analysis of myocardial collagen content. In an embodiment, a modified version of the photometric assay was employed in this study, by using picrosirius red instead of a trichrome stain. Picrosirius red exclusively polarizes collagen allowing for more objective identification of collagen. This benefit is reflected in the calculated intra- and inter-observer concordance (r=0.99 and 0.99 respectively).

Once the preserved myocardial slices were stained, the sections of interest were identified. Each area of interest was subdivided into quadrants. Within each quadrant, 16 digital photos were taken under 40× magnification. Each photo represented 2.5 mm$^2$; therefore, 40 mm$^2$ were analyzed from each section. This allows for a representative sampling of CVF.

Collagen, easily identified by polarizing light, was manually traced by a mouse pad. This step was repeated for stained muscle and the area determined in a similar fashion. CVF was then obtained for each section by the following equation:

$$\text{CVF} = \text{Connective tissue pixel count in 16 fields/Total pixel count in 16 fields} \quad (3)$$

Analysis of variance was used for comparison of CVF and the myocardial partition coefficient across tissue sample classifications. Tukey's Honest Significant Difference for multiple comparisons was used to evaluate significance for differences between individual data points. Linear regression analysis was used to determine the association between the myocardial partition coefficient and CVF. All statistical analysis was performed with R (R Foundation for Statistical Computing, Vienna, Austria. ISBN 3-900051-07-0, URL http://www.R-project.org). A p-value of 0.05 was used as a cut-off to determine statistical significance.

The mean values of CVF were significantly different based on histological classification i.e. normal myocardium vs. interstitial fibrosis vs. replacement fibrosis (p=0.015). Analysis of variance with adjustment for multiple comparisons indicated significant differences in CVF between normal samples and those with replacement fibrosis (p=0.012); but not for normal vs. interstitial (p=0.45), and also not for interstitial vs. replacement (p=0.19, FIG. 3B). Specifically, the mean values with corresponding 95% confidence intervals for replacement fibrosis, interstitial fibrosis and normal myocardium were 4.1%+/−0.23; 2.3%+/−0.23; and 1.3%+/−0.26, respectively.

Figure 3A:
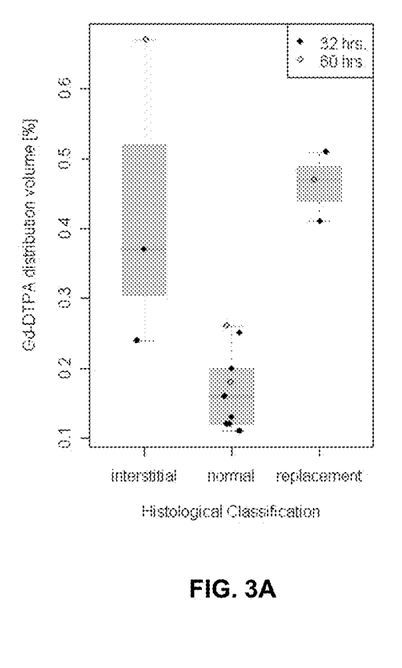
FIGS. 3A and 3B illustrate tissue samples stained and viewed under polarized light and classified as normal, or showing interstitial or replacement fibrosis, respectively. The measured gadodiamide distribution volumes, and CVFs for these three classifications, are shown (boxes show 25% and 75% percentile limits). The points represent the measured values, and the gadodiamide distribution volume. Open circles represent the samples that remained unthawed for 60 hours. Closed circles represent samples that remained unthawed for 32 hours.
Figure 3B:
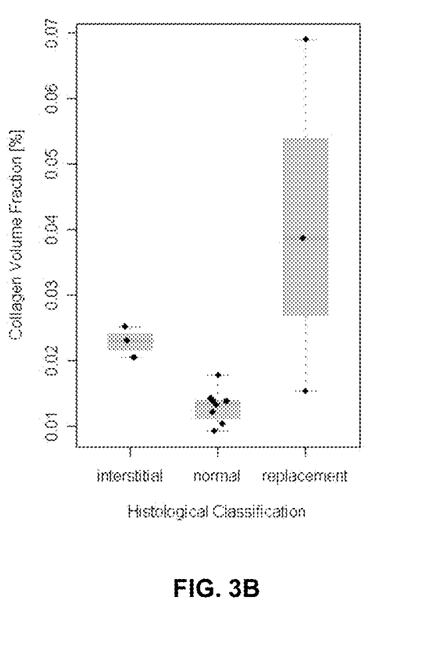

Similarly, mean values of gadodiamide distribution volume were significantly different based on histological classification i.e. normal myocardium vs. interstitial fibrosis vs. replacement fibrosis (p=0.001, FIG. 3A). Specifically, mean values of distribution volume with corresponding 95% confidence intervals for replacement fibrosis, interstitial fibrosis, and normal myocardium were 0.46+/−0.05, 0.43+/−0.22 and 0.17+/−0.05, respectively. Analysis of variance with adjustment for multiple comparisons indicated significant differences in gadodiamide distribution volume between normal samples vs. those with replacement fibrosis (p=0.003); between normal vs. interstitial fibrosis (p=0.007); but no significant difference for interstitial fibrosis vs. replacement fibrosis (p=0.90).

Figure 4:
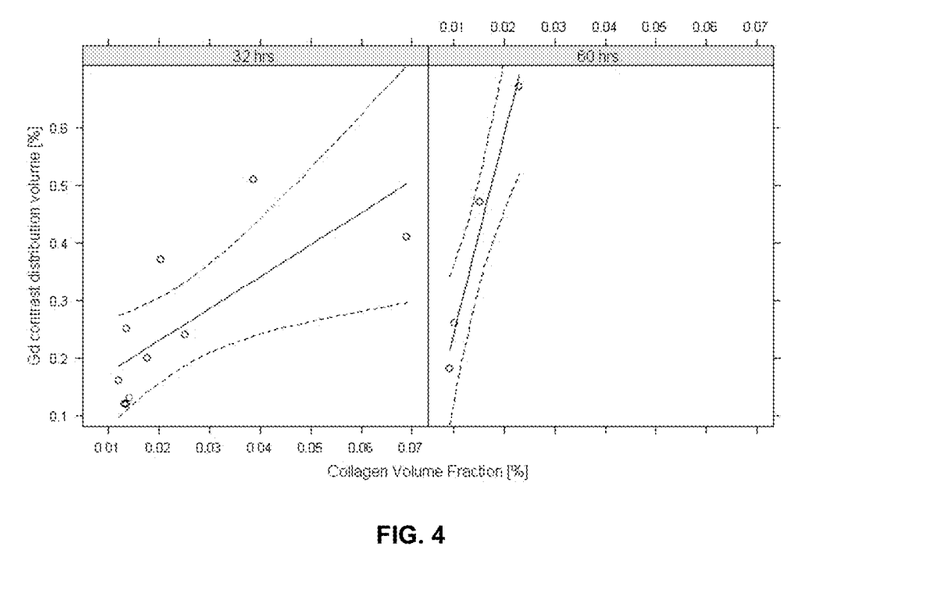
FIG. 4 provides a graph showing that the gadodiamide distribution volume in myocardial tissue correlated closely (measured at 32 hours after thawing of the heart sample) with the CVF ($r=0.727$; $p=0.017$). For the graph on the right, the correlation between gadodiamide distribution volume and CVF ($r=0.987$; $p=0.012$) is represented. The two graphs show different slopes based on the time lag between thawing of the sample and the post-contrast MRI measurement. Longer lag times increase cell membrane breakdown and therefore gadodiamide distribution volume is larger for the series of measurements with longer sample incubation times. The dotted lines in the graphs show the 95% confidence limits.

Measured values for CVF and gadodiamide distribution volume were found to be closely correlated (FIG. 4). The two graphs in FIG. 4 represent the results for each of two batches of samples. Each batch had a different thawing time. The left panel in FIG. 4 for samples thawed for 32 hours shows the correlation between gadodiamide distribution volume and CVF (Pearson correlation r=0.73; p=0.017). Likewise, the graph on the right, for samples thawed for 60 hours, shows a correlation of r=0.99 (p=0.012). Interestingly, the slopes of the two are different based on the time lag between thawing of the sample and the post-contrast MRI measurement.

A strong positive correlation between CVF and gadodiamide-MRI is shown in FIG. 4. While the findings were consistent with either thawing time, longer times likely increased gadodiamide distribution volume due to increased cell membrane breakdown, thus increasing the slope of the regression line. A more uniform distribution of gadodiamide in the tissue samples after 60 hours may account in part for the better correlation of the apparent gadodiamide distribution volume with the CVF, compared to the samples incubated in gadodiamide-saline solution for 32 hours.

Figure 5:
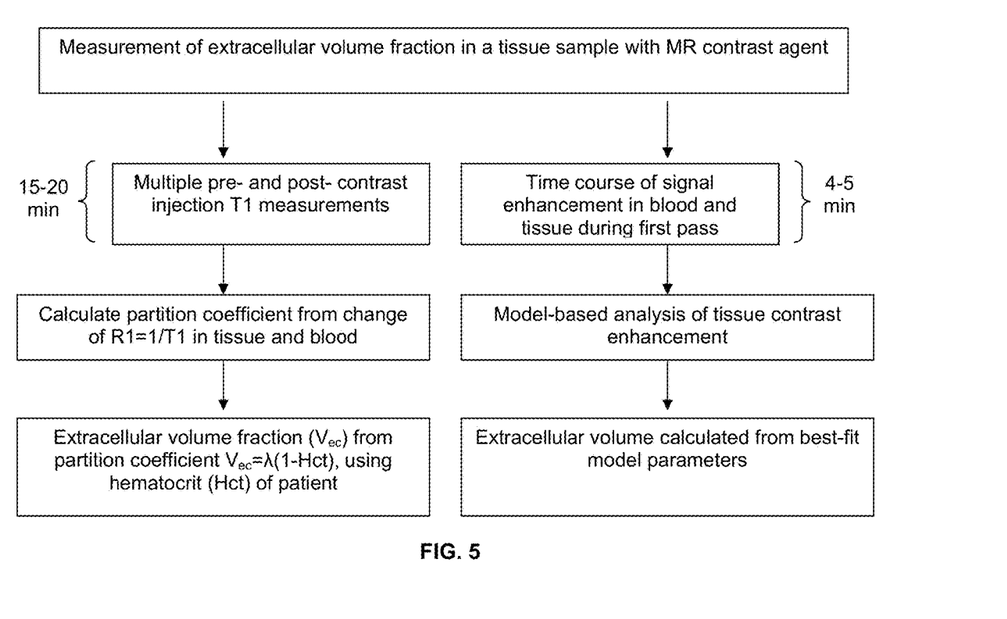
FIG. 5 is a flowchart outlining methods of measuring extracellular-volume fractions in accordance with embodiments.

FIG. 5 is a flowchart outlining various methods of measuring extracellular-volume fractions in accordance with embodiments. In embodiments, measurements may be obtained of an extracellular volume fraction in a tissue sample with an MR contrast agent. In an embodiment, multiple pre- and post-contrast injection T1 measurements may be obtained. Such an operation may be performed over an exemplary period of approximately 15-20 minutes. Further, the partition coefficient may be calculated from the change of R1=1/T1 in tissue and blood. Then, in an embodiment, the extracellular volume fraction ($V_{ec}$) may be calculated from the partition coefficient $V_{ec}=\lambda(1-\text{Hct})$, using hematocrit (Hct) of the patient. Thus, in an embodiment, a plurality of T1 relaxation time measurements may be performed in blood and in the sample, both before and after contact with one or more contrast agents to determine the tissue sample partition coefficient for the extracellular contrast agent. The relaxation times (T1) may be converted into relaxation rates with R1=1/T1, and each R1 rate determined for the sample may be linearly regressed against a determined R1 rate in the blood. In an embodiment, a blood hematocrit may be obtained, and the sample partition coefficient and the blood hematocrit may be used to calculate the extracellular volume in the tissue sample.

In an alternative embodiment, the time course of signal enhancement in blood and tissue may be determined during a first pass. Such an operation may be performed over an exemplary period of approximately 4-5 minutes. A model-based analysis of tissue contrast enhancement may be performed, and then an extracellular volume calculated from best-fit model parameters. Thus, in an embodiment, rapid imaging before, during and after contrast agent contact may be performed to measure contrast enhancement in the sample and in blood resident in a ventricular cavity or one or more large vessels. In an embodiment, the dynamics of contrast enhancement may be analyzed with a two-space model to determine the extracellular volume in the sample.

Figure 6A:
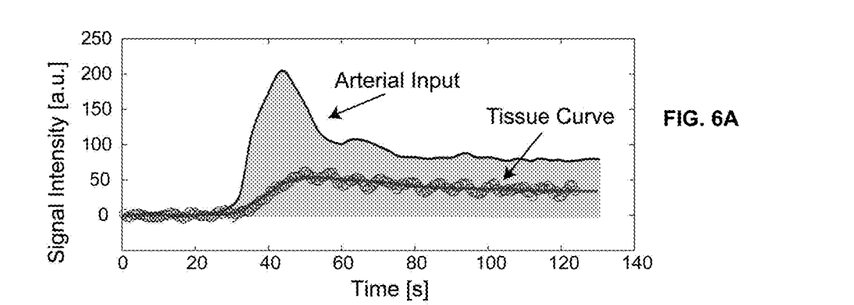
FIGS. 6A and 6B provide output graphs of methods of performing rapid imaging before, during and after contrast agent contact to measure contrast enhancement in the sample and in blood resident in a ventricular cavity or one or more large vessels in accordance with an embodiment.
Figure 6B:
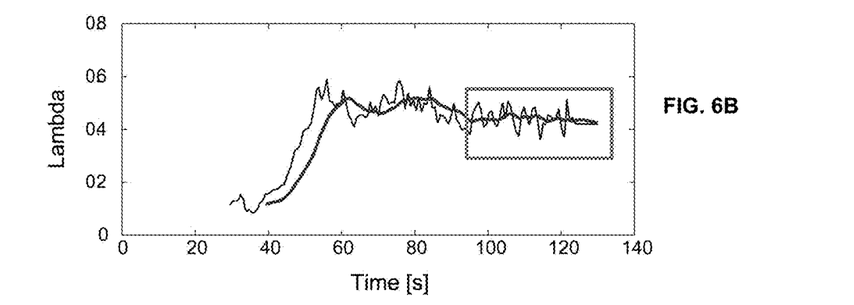

FIGS. 6A and 6B provide output graphs of methods of performing rapid imaging before, during and after contrast agent contact to measure contrast enhancement in the sample and in blood resident in a ventricular cavity or one or more large vessels in accordance with an embodiment. For such a method, images of the heart may be acquired rapidly during the first pass of an injected extracellular contrast agent, resulting in signal intensity changes in the blood pool of the left ventricular cavity ("arterial input") and in myocardial tissue as shown in FIG. 6A. An initial peak in the arterial input may be observed during the first pass of the contrast agent, followed by recirculation and approximation to a semi-equilibrium state. During this later phase of semi-equilibrium, one may take the ratio of signal intensities for the myocardial tissue and the arterial input to determine the partition coefficient. Applying this calculation to the data in FIG. 6A, results in the first (more variable) curve in FIG. 6B. For the partition coefficient calculation, one may also take a running average (the second (smooth) curve in FIG. 6B) and estimate the partition coefficient when concentration in the blood pool is in semi-equilibrium. A window representing a suitable semi-equilibrium is outlined by the small box in FIG. 6B. In an embodiment, one may also use a tracer kinetic model and correct the estimate of the partition coefficient for any variations of the arterial input.

There are several important heart diseases/conditions for which qualitative and quantitative measurements of myocardial fibrosis would be valuable for diagnosis and/or risk assessment, including (1) the broad category of heart failure that results from a variety of conditions ranging from familial disorders to myocardial infarction, (2) patients who will suffer sudden cardiac arrest in the future, which again may result from a spectrum of heart conditions, and (3) congenital heart disease, comprising several distinct disorders eventually having a component of myocardial fibrosis. In both ischemic and non-ischemic heart diseases, fibrosis often plays an important role. Even with healthy aging, diffuse fibrosis may be the underlying cause of stiffening of the ventricles which may be an important contributor toward diastolic dysfunction.

Prior methods utilize biopsies to obtain an indication of fibrosis, but biopsies are simply localized samples that do not provide a reliable indication of the overall (global) fibrosis burden. Thus, embodiments herein provide an imaging-based test to analyze diffuse fibrosis to determine the global fibrosis burden. Such an analysis provides important information to help in planning suitable treatment.

In accordance with an embodiment, a positive correlation between the methodology presented herein and the amount(s) of myocardial fibrosis for both interstitial as well as replacement fibrosis has been shown. In another embodiment, the present methods may be helpful in risk stratification for sudden cardiac death as well as disease severity of the conditions identified above.

Thus, embodiments may be used to correlate a determination of the presence of, location of, or extent of fibrosis in a tissue sample or whole heart with a heart condition, disease, or associated risk of a particular heart disease or failure. In an embodiment, a determined amount and/or location of myocardial fibrosis may be correlated to the risk of heart disease or failure. In an embodiment, a risk factor, such as a numeric or textual risk factor, may be assigned reflecting the extent and/or location of myocardial fibrosis (i.e., a scaled number, a percentage, a textual indicator such as high, medium, low, etc.). For example, in an embodiment, a higher amount of fibrosis (such as represented as a percentage of fibrotic tissue to healthy tissue) may result in a higher risk factor. In embodiments, other factors may be included in the analysis, such as age of the patient, other health conditions, etc.

Any one or more of various embodiments as previously discussed may be incorporated, in part or in whole, into an apparatus or system. In various embodiments an apparatus or system may comprise a server or other computing device, a storage medium and a plurality of programming instructions stored in the storage medium. In various ones of these embodiments, the programming instructions may be adapted to program an apparatus to enable the apparatus to perform one or more of the previously-discussed methods. For example, the programming instructions may be adapted to program an apparatus to enable the apparatus to perform image acquisition and/or analysis.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the intended scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of distinguishing normal myocardium from viable myocardium with diffuse interstitial and/or replacement fibrosis in heart tissue, comprising:

selecting a sample comprising viable heart tissue;

obtaining, with a magnetic resonance imaging device, a plurality of measurements of T1 relaxation time in blood and in an extracellular component of the heart tissue before contacting the sample with an extracellular contrast agent;

contacting the sample with the extracellular contrast agent;

obtaining, with the magnetic resonance imaging device, a plurality of measurements of T1 relaxation time in blood and in the extracellular component of the sample, after contact with the extracellular contrast agent and wherein the extracellular contrast agent is at equilibrium between the blood and the extracellular component of the heart tissue;

converting the relaxation times (T1) into relaxation rates with $R1=1/T1$; and linearly regressing each R1 rate determined for the viable heart tissue against a R1 rate determined for the blood;

quantifying a myocardial partition coefficient for the extracellular contrast agent in the viable heart tissue using the T1 relaxation time measurements in blood and in the extracellular component of the heart tissue before and after contacting the sample with the extracellular contrast agent;

obtaining a blood hematocrit level;

calculating the extracellular volume in the tissue sample using the myocardial partition coefficient partition coefficient and the blood hematocrit level; and determining an extracellular volume fraction of the contrast agent to distinguish normal myocardium from viable myocardium with diffuse interstitial and/or replacement fibrosis.

2. The method of claim 1, wherein contacting the sample with the extracellular contrast agent comprises contacting the sample with a Gadolinium-containing contrast agent.

3. The method of claim 1, wherein contacting the sample with the extracellular contrast agent comprises contacting the sample with gadodiamide.

4. The method of claim 1, wherein contacting the sample with the extracellular contrast agent comprises contacting the sample in-vivo with the extracellular contrast agent.

5. The method of claim 1, wherein contacting the sample with the extracellular contrast agent comprises contacting the sample in-vitro with the extracellular contrast agent.

6. The method of claim 1, further comprising determining a global diffuse fibrosis burden in the sample.

7. The method of claim 1, further comprising classifying an extent of diffuse fibrosis in a patient from which the sample is selected to determine risk of heart failure or heart disease.

8. The method of claim 1, further comprising determining and distinguishing between an extent of interstitial and an extent of replacement fibrosis in the sample.

9. The method of claim 1, further comprising obtaining one or more images of the sample using computed x-ray tomography.

10. The method of claim 1, further comprising determining the presence of, location of, and/or extent of interstitial and replacement fibrosis in a tissue sample or whole heart and correlating the determination with a heart condition, disease, or associated risk of a particular heart disease or failure.

11. The method of claim 10, wherein correlating the determination with a heart condition, disease, or associated risk of a particular heart disease or failure is represented as a numeric or textual risk factor.

* * * * *